United States Patent
Fendler et al.

(10) Patent No.: US 6,333,039 B1
(45) Date of Patent: Dec. 25, 2001

(54) OPAQUE SKIN SANITIZING COMPOSITION

(75) Inventors: Eleanor J. Fendler, Hudson; Lois V. Dunkerton, Maumee; Aija Zirnis, Solon, all of OH (US)

(73) Assignee: GOJO Industries, Inc., Akron, OH (US)

( * ) Notice: Subject to any disclaimer, the term of this patent is extended or adjusted under 35 U.S.C. 154(b) by 0 days.

(21) Appl. No.: 09/160,980

(22) Filed: Sep. 25, 1998

(51) Int. Cl.$^7$ ................................ A61K 7/48; A61K 7/50
(52) U.S. Cl. ..................... 424/401; 424/405; 424/414; 424/420; 428/537.5
(58) Field of Search ................................ 424/401, 405, 424/414, 420; 728/537.5

(56) References Cited

U.S. PATENT DOCUMENTS

| | | | |
|---|---|---|---|
| 5,243,021 | 9/1993 | Langer et al. | 528/272 |
| 5,246,613 | 9/1993 | Gilbert et al. | 252/117 |
| 5,250,652 | 10/1993 | Langer et al. | 528/125 |
| 5,294,438 | 3/1994 | Chang et al. | 424/73 |
| 5,385,685 | 1/1995 | Humphreys et al. | 252/174.17 |
| 5,389,279 | 2/1995 | Au et al. | 252/108 |
| 5,508,029 | 4/1996 | Petchul et al. | 424/78.07 |
| 5,538,740 | 7/1996 | Abad | 424/547 |
| 5,629,006 | 5/1997 | Hoang et al. | 424/405 |
| 5,658,559 | 8/1997 | Smith | 424/78.02 |
| 5,698,183 | 12/1997 | Langer et al. | 424/59 |
| 5,703,026 | 12/1997 | Setser et al. | 510/152 |
| 5,716,920 | 2/1998 | Glenn, Jr. et al. | 510/159 |
| 5,908,707 | * 6/1999 | Cabell et al. | 428/537.5 |

FOREIGN PATENT DOCUMENTS

08169809 * 7/1996 (JP).

OTHER PUBLICATIONS

English Translation of JP 8–169809 pp. 1–11, Jul. 1996.*
HCAPLUS Abstract No. 1996:537065 of JP 8–169809, Jul. 1996.*

* cited by examiner

*Primary Examiner*—Bennett Celsa
(74) *Attorney, Agent, or Firm*—Reese Taylor

(57) ABSTRACT

A skin sanitizing composition includes an effective amount of an alcohol having 1 to 4 carbon atoms for providing sanitizing activity to the sanitizing composition as well as an effective amount of at least one moisturizing agent having opacifying properties for both making the sanitizing composition uniformly opaque when mixed and reducing water loss from the skin. The composition also includes an effective amount of a polymeric thickener for providing a viscosity of from about 1000 to about 65,000 cps and water.

14 Claims, No Drawings

OPAQUE SKIN SANITIZING COMPOSITION

TECHNICAL FIELD

The present invention relates generally to a sanitizing composition for the skin. More particularly, the present invention relates to a skin sanitizing composition containing a lower alkanol as the active antimicrobial ingredient, a moisturizing agent that is also an opacifier, a thickening agent, and water.

BACKGROUND OF THE INVENTION

Skin disinfecting or sanitizing compositions have become increasingly popular in the health care industry as well as with the general public for providing antimicrobial effectiveness to the skin without irritation. Generally, these skin disinfecting or sanitizing compositions, which should be distinguished from skin cleansing compositions such as soaps, shampoos, and detergents which typically include surfactants, abrasives, or other active ingredients used to physically as well as microscopically cleanse the skin, include alcohol as the active ingredient in killing any microorganisms which may be present on the skin, particularly the hands. Unfortunately, several misconceptions have evolved with the use of these skin disinfecting or sanitizing compositions. For instance, one common misconception is that these compositions will kill all bacteria or microorganisms instantly. In actuality, many of these skin disinfecting or sanitizing compositions require that the user maintains the alcohol-based composition on the skin for a period of time in order for the alcohol to effectively kill the bacteria or other microorganisms which might be present on the skin. Typically, it is recommended that the compositions not be removed from the skin for at least ten to fifteen seconds in order to allow the antimicrobial agent, e.g., alcohol, sufficient time to kill the microorganism.

Another misconception is in determining the amount of skin disinfecting or sanitizing composition needed for a thorough and effective disinfecting of the skin, particularly the hands. An effective amount of the antimicrobial composition will enable the user to spread the alcohol via rubbing together of the hands to completely cover the entirety of the hands. Oftentimes, a user will only obtain enough of the composition to disinfect a portion of the hands, leaving other areas of the hands still potentially infected with the bacteria or other microorganisms. This is particularly true where the sanitizing compositions are translucent and clear because it is virtually impossible for the user to determine whether or not the skin has been effectively covered. Moreover, given the relatively careless handwashing procedures used by individuals, particularly children, today, it is believed common for the user to miss entire areas of the skin where bacteria or other microorganisms might live on the skin.

On the other hand, too much of an alcohol-based composition is rough on the skin. Although alcohol is generally recognized as a very effective antimicrobial agent and is often noted as being relatively "mild" to the skin as compared to other active antimicrobial ingredients, continuous use of alcohol-based compositions, without protecting the skin, will ultimately dry out the skin, causing it to chap or crack.

Therefore, it is believed important to provide moisturizing properties to the skin, preferably at the same time the alcohol is being utilized. The defatting nature of alcohol to the skin requires that moisturizing agents or other skin conditioning agents be used to reduce water loss from the skin. Thus, moisturizers are sometimes used to provide skin conditioning benefits and improve mildness to the skin. Oftentimes, emollients are used as the moisturizers which essentially impart a smooth and soft feeling to the skin surface, but may or may not reduce water loss. Emollients also can refat the skin to reverse the defatting nature of alcohol.

At present, there are essentially two, and possibly three, ways of reducing water loss from the skin. One way is to deposit on the skin surface an occlusive layer which reduces the rate of evaporation. This method, however, often leaves an undesirable film on the skin.

The second way is to add non-occlusive hygroscopic substances to the skin which will retain water and make this water available to the skin to alter its physical properties and produce a cosmetically desirable effect. Non-occlusive moisturizers may also function by improving the lubricity of the skin.

A potential third way is to reduce the rate of evaporation from the skin by improving the barrier function of the skin. This potentially could be done through the use of agents to change the physical structure of the skin.

Thus, the need exists for an alcohol-based sanitizing composition which includes at least one moisturizing agent capable of not only reducing the water loss of the skin but also-serving as an opacifier for the composition which will effectively make the composition opaque such that the user of the composition will readily be able to determine the amount of sanitizing composition deposited on the skin and to determine when the composition has been completely spread over the entirety of the skin. An opaque sanitizing composition will also enable the user to determine how long the composition has been on the skin before wiping the composition away or having it evaporate.

A number of patents have cited the use of alcohol as an active ingredient for providing skin disinfecting properties to a skin cleansing composition. For example, U.S. Pat. No. 5,629,006 teaches a skin disinfecting formulation comprising alcohol and a surfactant-like block copolymer, namely a polyalkylene oxide/polydimethylsiloxane copolymer. This patent also discloses the use of thickeners such as celluloses, carbomers, pluronics, etc., and preservative antimicrobial agents such as p-chloro-m-xylenol. However, neither these patents nor any other known patent which includes alcohol as an active disinfecting or sanitizing ingredient teach or suggest which also functions as an opacifier.

There are, however, some patents which include opacifying agents as an optional ingredient in their cleansing compositions. For example, U.S. Pat. Nos. 5,243,021, 5,250,652, 5,385,685, 5,389,279, and 5,698,183 each disclose personal care products such as facial or body cleansing compositions which also include moisturizers to provide conditioning to the skin. It will be appreciated, however, that each of these personal care products include necessary cleansing surfactants and do not suggest using opacifiers. On the other hand, opacifiers discussed in these patents for light duty liquid detergent compositions where moisturizers are wholly unnecessary and which are not used directly on the skin. Thus, it has not been heretofore suggested that an opacifier be used that also functions as part of the moisturizing system of the composition.

DISCLOSURE OF THE INVENTION

It is, therefore, an object of the present invention to provide a skin sanitizing composition.

It is another object of the present invention to provide a skin sanitizing composition, as above, which is opaque, particularly when applied to the skin.

It is still another object of the present invention to provide a skin sanitizing composition, as above, which uses a lower alcohol as the active antimicrobial ingredient.

It is yet another object of the present invention to provide an alcohol-based skin sanitizing composition, as above, wherein at least one moisturizing agent also functions as an opacifier, or vice versa, an opacifying agent also functions as part of the moisturizing system.

These and other objects of the present invention, as well as the advantages thereof over existing prior art relating to skin sanitizing compositions, which will become apparent from the description to follow, are accomplished by the improvements hereinafter described and claimed.

In general, an opaque skin sanitizing composition for application to skin, prepared in accordance with one or more aspects of the present invention, includes an effective amount of an alcohol having 1 to 4 carbon atoms for providing sanitizing activity to the sanitizing composition; an effective amount of at least one moisturizing agent having opacifying properties for both making the sanitizing composition uniformly opaque and reducing the rate of water loss from the skin; an effective amount of a polymeric thickener for providing a viscosity to the composition of from about 1000 to about 65,000 cps; and water.

Other aspects of the present invention are provided by an opaque skin sanitizing composition for application to skin containing at least about 50 weight percent of an alcohol having 1 to 4 carbon atoms; from about 0.1 to about 5 weight percent of at least one moisturizing agent having opacifying properties for both making the sanitizing composition uniformly opaque and reducing water loss from the skin; from about 0.1 to about 10 weight percent of at least a second moisturizing agent not having said opacifying properties; from about 0.05 to about 2 weight percent of a thickener; and the balance, water.

A preferred exemplary skin sanitizing composition incorporating the concepts of the present invention is shown by way of example in the detailed description of the preferred embodiments without attempting to provide all the various forms and modifications in which the invention might be embodied, the invention being measured by the appended claims and not by the details of the specification.

PREFERRED EMBODIMENT FOR CARRYING OUT THE INVENTION

The present invention is directed toward an opaque sanitizing composition comprising an alcohol as the active sanitizing or antimicrobial ingredient and at least one moisturizing agent which also acts as an opacifying agent. The sanitizing composition has been particularly formulated with a polymeric thickener and water for preferably topical application to skin, and more particularly, to the hands.

An alcohol is preferably used in the skin sanitizing composition for its antimicrobial properties. It kills gram-positive and gram-negative bacteria, fungi, and many viruses. The potent activity of alcohol against microorganisms is believed due to its denaturation of proteins and enzymes and dehydration. Generally, a concentration of alcohol of at least about 20 percent by weight, and more preferably, about 50 percent by weight of the composition is an effective amount for providing antimicrobial activity to the composition, although more or less alcohol may be required in certain instances, depending particularly on other ingredients and/or the amounts thereof employed in the composition.

Preferably, a lower alkanol is used as the alcohol. Such alcohols include, but are not limited to, methanol, ethanol, propanol, isopropanol, butanol, isobutanol and tertiary butanol. An alcohol containing 1 to 4 carbon atoms is more preferred, with ethanol being the most preferred alcohol for the preferred embodiment of the subject composition. The preferred alcohols are more preferably used in an amount ranging from about 20 weight percent to about 80 weight percent, and most preferably, from about 50 weight percent to about 70 weight percent.

It will be appreciated that alcohol, as used in the present invention, is not intended as a solvent or carrier for some other ingredients, e.g., surfactants, abrasives, etc., which may affect the nature of the invention. Rather, alcohol is employed as the preferred sanitizing or antimicrobial agent, and the composition preferably contains no abrasives or surfactants which provide for physical cleansing of the skin. While it is most preferred that no surfactants be used in the present invention, only those surfactants which aid in or provide for the physical cleansing of the skin are generally, preferably prohibited.

In addition, it is most preferred that alcohol be the only active antimicrobial ingredient introduced into the composition. However, it is noted that the composition may optionally contain certain other sanitizing or antimicrobial agents in addition to alcohol which might provide some residual antimicrobial efficacy. These other antimicrobial agents include, but are not limited to, triclosan also known as 5-chloro-2(2,4-dichlorophenoxy) phenol and available from Ciba-Geigy Corporation under the tradename IRGASAN; chloroxylenol also known as 4-chloro-3,5-xylenol and available from Nipa Laboratories, Inc. under the tradenames NIPACIDE MX or PX; hexetidine also known as 5-amino-1,3-bis(2-ethylhexyl)-5-methyl-hexahydropyrimidine; chlorhexidine salts including chlorhexidine gluconate and the salts of N,N"-Bis(4-chlorophenyl)-3,12-diimino-2,4,11,14-tetraazatetradecanediimidiamide; 2-bromo-2-nitropropane-1; 3-diol, benzalkonium chloride; cetylpyridinium chloride; alkylbenzyldimethylammonium chlorides; iodine; phenol derivatives, povidone-iodine including polyvinylpyrrolidinone-iodine; parabens; hydantoins and derivatives thereof, including 2,4-imidazolidinedione and derivatives of 2,4-imidazolidinedione as well as dimethylol-5,5-dimethylhydantoin (also known as DMDM hydantoin or glydant); phenoxyethanol; cis isomer of 1-(3-chloroallyl)-3,5,6-triaza-1-azoniaadamantane chloride, also known as quaternium-15and available from Dow Chemical Company under the tradename DOWCIL 2000; diazolidinyl urea; benzethonium chloride; methylbenzethonium chloride; and mixtures thereof. Most preferred of these antimicrobial agents are triclosan, chloroxylenol and chlorhexidine gluconate. These antimicrobial agents are more preferably used in only minor amounts of from about 0.1 to about 1 percent by weight and, as such, they may be viewed as preservatives rather than active ingredients.

The composition also contains at least one moisturizer. More than one moisturizing agent may be used in the composition of the present invention, but at least one of the moisturizers should also be an opacifying agent. The preferred opacifying moisturizers are selected from the group consisting of polyethylene, polypropylene, and sodium styrene-based copolymers. Particularly suitable for use as the opacifying moisturizers in the present invention are a series of opacifying copolymers containing a sodium derivative of a styrene monomer available from Morton International. These copolymers may be available from Morton under the tradename LYTRON or OPACIFIER and include, but are not necessarily limited to, sodium styrene/acrylates copolymer, sodium styrene acrylates/divinyl benzene, sodium styrene/acrylates/PEG 10, sodium styrene/acrylates/ PEG 10 maleate/nonoxynol 10 maleate, sodium styrene/ acrylamide, and sodium styrene/sodium methacrylate. Most preferred are the sodium styrene/acrylates copolymer available under the tradename OPACIFIER 653. While the opacifying character of these copolymers have been well documented, their use as moisturizing agents has not been heretofore recognized in the art.

Particularly suitable polyethylenes and polypropylenes include homopolymers and waxes thereof, including oxidized derivatives thereof, available from Petrolite Corp. of Tulsa, Okla., under the tradenames POLYWAX or PETROLITE. Other polyethylene or polypropylene homopolymers and waxes are available from Eastman Chemical Co. of Kingsport, Tenn., under the tradename EPOLENE, from Hoechst under the tradename HOECHST WAX, and from Union Carbide under the tradename CARBOWAX.

These opacifying moisturizing agents are preferably used in effective amounts suitable for making the resultant sanitizing composition uniformly opaque upon proper mixing and to reduce the rate of water loss from the skin upon application of the sanitizing composition. Typically, from about 0.1 weight percent to about 5 weight percent, and more preferably, from about 0.2 weight percent to about 1 weight percent of the opacifying moisturizer is employed.

Other moisturizing agents which are not also opacifying agents may also be used in the present invention. Preferably, these moisturizers are, like the opacifying moisturizers, typically non-occlusive hygroscopic substances which retain water and make this water available to the skin. Some of these non-opacifying, non-occlusive moisturizers may be found naturally in the skin while others are not. Examples of such moisturizers include glycerin, water-soluble such as sorbitol, hydrolyzed proteins, urea, hydrolyzed starch, hydroxy acids such as lactic acid and fruit acids and salt derivatives thereof, pyrrolidone carboxylic acid, aloe vera gel, cucumber juice, mineral oils, squalene, and tocophenol. Preferably, these moisturizing agents, if used, are used in amounts effective for softening or moisturizing the skin, those amounts typically ranging from 0.1 to about 2 percent by weight.

Among the more preferred of these types of moisturizers is glycerin, a polyhydric alcohol that conforms generally to the formula

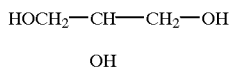

Glycerin is commonly used in personal care products for its humectant properties, but it is also recognized for its excellent moisturizing and softening properties.

Another suitable, optional moisturizing agent useful in the present invention is found in essentially nonvolatile silicone fluids. These silicone fluids may be a polyalkyl siloxane, a polyaryl siloxane, a polyalkylaryl siloxane or a polyether siloxane copolymer and, if used, is present in an amount effective to soften and moisten the skin, typically being used in ranges of from about 0.1 percent by weight to about 10 percent by weight. Examples of essentially nonvolatile polyalkyl siloxane fluids useful for the present invention include dimethicone and dimethiconol, such as is available under the tradename Dow Corning 1403 Fluid.

The composition of the present invention also includes an effective amount of a polymeric thickener to adjust the viscosity of the sanitizing composition, preferably to a viscosity range of from about 1000 to about 65,000 centipoises, to facilitate dispensing of the sanitizing composition conveniently onto the skin.

Examples of polymeric thickeners include cross-linked polyacrylic acids, polyacrylamides, carbomers, pluronics, celluloses, xanthan gums, guar gums, alginates, pectins, carrageenans, polyethylene glycol, polyvinyl alcohols, polyvinyl pyrrolidone, and modified starches.

One particular polymeric thickening agent useful in the composition is a cross-linked polyacrylic acid available from B. F. Goodrich Co. under the tradename Ultrez-10. Generally, carbomers are commercially acceptable thickeners due mainly to their excellent aesthetic feel and the ease with which they are mixed into such compositions. In addition, carbomers are generally used in lesser amounts than other thickeners to obtain essentially the same viscosity of the composition. Thus, carbomers are recognized as being very helpful in lowering the cost of manufacturing of these and related compositions.

Generally, the thickening agent may comprise from about 0.05 percent by weight to about 2 percent by weight, and more preferably, from about 0.1 percent to about 1 percent by weight of the composition, although as noted hereinabove, any amount effective to adjust the viscosity of the sanitizing composition to a viscosity range suitable for use as a skin sanitizing lotion, preferably to a viscosity range of from about 1000 to about 65,000 centipoises, is preferred.

The sanitizing compositions herein can contain a variety of other nonessential optional ingredients suitable for rendering such compositions more formulatable, or aesthetically and/or cosmetically acceptable. Such conventional optional ingredients are well known to those skilled in the art and include, but are not necessarily limited to, e.g., preservatives, pH adjusting or neutralizing agents, emollients, lubricity agents, perfumes, and dyes. These ingredients are typically used in minor, but effective, amounts well known to those skilled in the art, typically on the order of less than 1 percent by weight.

Emollients are often used to impart a smooth and soft feeling to the skin surface in much the same way as the moisturizers discussed hereinabove. However, emollients differ from the moisturizers discussed herein in that they impart a smooth and soft feel to the skin without measurably affecting the skin hydration level and or the skin lipid barrier. Examples of such emollients include vegetable triglycerides, such as avocado oil, olive oil, sunflower seed oil, organic acid esters such as sorbitan oleate, myristyl myristate, isopropyl myristate, and glyceryl oleate.

The composition can also optionally include a preservative to prevent microbial spoilage. Examples of preservatives include essentially the same list of optional antimicrobial agents described hereinabove, used in minor amounts. Other examples of preservatives include, but are not limited to, iodopropynyl butylcarbamate, imidazolidinyl urea, methylchloroisothiazolinone and methylisothiazolinone. These preservatives, as well as the preferred examples of antimicrobial agents, including triclosan, chloroxylenol, and chlorhexidene gluconate, may often be used in minor amounts (less than 1 percent by weight) as preservatives for the subject compositions.

A lubricity agent also generally aids in creating a soft and smooth feel to the compositio en the hands. An example of a lubricity agent useful in the present invention is a benzoic acid ester of a $C_{12}$–$C_{15}$ alcohol such as is available under the tradename Finsolv TN. Other lubricity agents may include volatile silicones such as cyclomethicone tetramer and pentamer (available from Dow Corning as Dow Corning 244 or 245 Fluids) or non-volatile silicones such as stearyl dimethicone (available from Dow Corning as Dow Corning 2503 Cosmetic Wax).

A pH adjusting or neutralizing agent is commonly used to adjust the acidity of the composition to a desirable range, typically to a pH of about 6 to 8. As the composition will typically be somewhat acidic, the neutralizing agent will tend to be slightly basic. One example of a suitable neutralizing agent is aminornethylpropanol. This agent is typically added in an amount effective to change the pH of the composition to the desired pH range. Generally, this neutralizing agent comprises less that 0.4 weight percent of the total composition.

It will be appreciated that the remaining percentage or balance of the composition is water. Water acts as a vehicle to ensue even distribution of the composition to the skin. Notably, no additional ingredients are added to the composition as opacifying agents, the opaqueness of the composition resting upon the use of the opacifying moisturizers set forth hereinabove.

In a preferred embodiment, the skin sanitizing composition is prepared by first dispersing the polymeric thickening agent in water with strong agitation for at least about 45 minutes. Next, alcohol is added to the composite mix and a preservative, if any, is added, and the mix is agitated until the preservative is completely dissolved. This should take about 45 minutes. Next, the other ingredients are added, and the mix is agitated until the opacifying moisturizer is uniformly dispersed. The composition, which is typically somewhat acidic, is neutralized with the neutralizing agent to about pH in the range of about 6 to 8.25. The composition is further agitated until uniform throughout.

Preferably, the viscosity of the composition may range from about 10,000 to about 65,000 cps (LVF 4, speed 12, 70° F.), but the top and bottom viscosity should remain within about 300 cps of each other.

In order to demonstrate practice of the present invention, a sample of the preferred sanitizing lotion composition was prepared by first dispersing, by way of sprinkling, approximately 4 grams of the thickener, Ultrez-10, into about 329 grams of process water with rapid agitation. The polymer was allowed to hydrate with agitation at ambient temperature for about 40 minutes. Approximately 645 grams of specially denatured alcohol (190 proof) was then added to the composite mixture. Then, about 2 grams of pellets of a preservative (glyceryl laurate available from Med-Chem Labs, Inc. of East Lansing, Mich. under the tradename LAURICIN), was added, and the mixture agitated for another approximate 40 minutes until all the pellets were dissolved. Coloring dyes (FD&C Red and Yellow) were added until a peach color was obtained. Next, about 4 grams of the lubricity agent, Finsolv TN was added along with about 1.3 grams of fragrance, about 2.5 grams of glycerin, about 0.01 grams of propylene glycol, about 0.01 grams of isopropyl myristate, 0.001 grams of tocopheryl acetate and vitamin A palmitate, about 8 grams of a non-volatile silicone fluid, namely Dow Corning 1403 Fluid, and about 7 grams of the opacifying moisturizer, OPACIFIER 653. The mixture was then agitated until uniform in opaqueness and consistency. The pH of the composite mixture was adjusted to 7.2 by addition of 1.27 grams of aminomethylpropanol. The mixture was gently agitated for another 10 minutes and then poured into suitable containers.

Once the composition was prepared, a commonly used bioengineering technique was utilized to determine the skin moisturizing capabilities of the prepared sample. The bioengineering technique employed measures the hydration (i.e., moisture content) of the stratum corneum of the skin. A Corneometer model TC-350® (Courage and Khazaka, Cologne, Germany) was used to determine the change in skin moisture content after successive applications or treatments of the composition to a particular area of skin. The corneometer measures the water content using a capacitance method. Standard methods were used for the measurements. For a more complete and detailed discussion and description of the standard methods employed for determining the skin moisture content of the stratum comeum, see E. Berardesca, "EEMCO Guidance for the Assessment of Stratum Corneum Hydration: Electrical Methods" *Skin Research and Technology*, 3, 126–132 (1997), hereby incorporated by reference.

The results of the skin moisturization study are shown in Table I hereinbelow.

TABLE I

Moisturization Study of Skin Hydration and Skin Moisture Capacity After Treatment of Skin

| | Moisture Content | | |
|---|---|---|---|
| | Treatment 1 | Treatment 2 | Treatment 3 |
| Skin Hydration | 2.84 | 5.84 | 7 |
| Skin Moisture Capacity | 6.68 | 11.26 | 11 |

The results of this study demonstrate a statistically significant increase in skin hydration and skin moisture capacity between the first and second application or treatment of the product relative to its baseline reading. Moreover, skin hydration continues to increase upon the successive applications of the sanitizing composition.

Thus, it should be evident that the skin sanitizing compositions of the present invention are highly effective in providing antimicrobial activity to the skin, while reducing water loss from the skin. The opaque skin sanitizing compositions also enable the user to employ the compositions with a more realistic idea of the amount necessary to be utilized and of the areas of skin being covered. The invention is particularly suitable for health care givers, but is not necessarily limited thereto. The compositions of the present invention can be used with other ingredients and agents including, but not limited to, UV absorbers such as benzophenone-4, solubilizers such as PEG-40 castor oil, chelating agents such as disodium EDTA, antioxidants such as 3-t-butyl-4-hydroxyanisole (BHA) and ascorbic acid, pearlizing agents, foaming agents, dyes, fragrances, beads, and other ingredients which do not materially effect the moisturizing, opacifying or antimicrobial nature of the composition.

Based upon the foregoing disclosure, it should now be apparent that the use of the composition described herein will carry out the objects set forth hereinabove. It is, therefore, to be understood that any variations evident fall within the scope of the claimed invention and, thus, the selection of specific components or ingredients can be determined without departing from the concepts or the spirit of the invention herein disclosed and described. Thus, the scope of the invention shall include all modifications and variations that may fall within the scope of the attached claims.

What is claimed is:

1. An opaque skin sanitizing composition comprising:
   at least about 50 weight percent of an alcohol having 1 to 4 carbon atoms;
   from about 0.1 to about 5 weight percent of at least one moisturizing agent having opacifying properties for both making the sanitizing compositions uniformly opaque and reducing water loss from the skin, said opacifirng moisturizer selected from the group consisting of polyethylene copolymers, polypropylene copolymers, and sodium styrene-based copolymers;

from about 0.1 to about 10 weight percent of at least a second moisturizing agent not having said opacifying properties;

from about 0.05 to about 2 weight percent of a thickener; and water.

2. The skin sanitizing composition according to claim 1, wherein said alcohol is selected from the group consisting of methanol, ethanol, propanol, isopropanol, butanol, isobutanol, and tertiary butanol.

3. The skin sanitizing composition according to claim 1, wherein said composition contains at least 50 weight percent alcohol.

4. The skin sanitizing composition according to claim 1, wherein said opacifying moisturizer is a copolymer selected from the group consisting of sodium styrene/acrylates, sodium styrene acrylates/divinyl benzene, sodium styrene/acrylates/PEG 10, maleate/nonoxynol 10 maleate, sodium styrene/acrylamide, and sodium styrene/sodium methacrylate.

5. The skin sanitizing composition according to claim 1, wherein said second moisturizer is selected from the group consisting of glycerin, water-soluble polyols, hydrolyzed proteins, urea, hydrolyzed starch, hydroxy acids, salts of hydroxy acids, pyrrolidone carboxylic acid, aloe vera gel, cucumber juice, mineral oils, squalene, and tocophenol.

6. The skin sanitizing composition according to claim 1, wherein the second moisturizer is a nonvolatile silicone fluid.

7. The skin sanitizing composition according to claim 1, wherein said thickener is selected from the group consisting of cross-linked polyacrylic acids, polyacrylamides, carbomers, pluronics, celluloses, xanthan gums, guar gums, alginates, pectins, carrageenans, polyethylene glycol, polyvinyl alcohols, polyvinyl pyrrolidone, and starches.

8. The skin sanitizing composition according to claim 1, further comprising at least one emollient selected from the group consisting of vegetable triglycerides, and organic acid esters.

9. The skin sanitizing composition according to claim 1, further comprising at least one preservative.

10. The skin sanitizing composition according to claim 1, further comprising an effective amount of at least one lubricity agent to aid in creating a soft and smooth feel to the composition.

11. The skin sanitizing composition according to claim 1, further comprising an effective amount of a neutralizing agent to neutralize the pH of the composition to between about 6 and about 8.25.

12. The skin sanitizing composition according to claim 1 further comprising at least one of a UV absorber, a solubilizer, castor oil, a chelating agent, an antioxidant, a pearlizing agent, a foaming agent, a dye, a fragrance, or beads.

13. An opaque skin sanitizing composition of claim 1, further comprising:

at least one emollient;

at least one preservative;

an effective amount of at least one lubricity agent to aid in creating a soft and smooth feel to the composition;

an effective amount of a neutralizing agent to neutralize the pH of the composition to between about 6 and 8.25;

at least one of a UV absorber, a solubilizer, castor oil, a chelating agent, an antioxidant, a pearlizing agent, a foaming agent, a dye, a fragrance, or beads.

14. The skin sanitizing composition according to claim 1, wherein said composition is devoid of surfactants that aid in the physical cleansing of the skin.

* * * * *